(12) United States Patent
Keenan et al.

(10) Patent No.: US 6,384,281 B1
(45) Date of Patent: May 7, 2002

(54) 3-BICYCLOARYL-2-AMINOMETHYL BICYCLOALKANES AS SEROTONINE REUPTAKE INHIBITORS

(75) Inventors: Martine Keenan, Hampshire; Sandra Ginette Milutinovic; David Edward Tupper, both of Bershire, all of (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/958,218

(22) PCT Filed: Apr. 6, 2000

(86) PCT No.: PCT/GB00/01294

§ 371 Date: Oct. 3, 2001

§ 102(e) Date: Oct. 3, 2001

(87) PCT Pub. No.: WO00/61539

PCT Pub. Date: Oct. 19, 2000

(30) Foreign Application Priority Data

Apr. 8, 1999 (GB) .............................................. 9908021

(51) Int. Cl.$^7$ .............................................. A61K 31/44
(52) U.S. Cl. .................. 564/428; 548/221; 548/490; 548/152; 548/525; 549/49; 549/58; 549/471; 549/462; 546/139; 546/152; 514/307; 514/311; 514/367; 514/415; 514/422; 514/444; 514/469; 514/65

(58) Field of Search .................................. 548/221, 490, 548/152, 525, 49, 58; 549/471, 462; 546/139, 152; 564/428; 514/307, 311, 367, 415, 422, 444, 469, 657

(56) References Cited

FOREIGN PATENT DOCUMENTS

| GB | 1549174 A | * | 8/1979 |
| GB | 1586249 A | * | 3/1981 |

* cited by examiner

*Primary Examiner*—Samuel Barts
(74) *Attorney, Agent, or Firm*—Paul J. Gaylo

(57) ABSTRACT

A pharmaceutical compound of formula (I) in which $R^1$ and $R^2$ are each hydrogen or $C_{1-4}$ alkyl, or $R^1$ and $R^2$ together with the nitrogen atom to which they are attached form an azetidinyl, pyrrolidinyl, piperidinyl, piperazinyl, or morpholino group, said group being optionally substituted with 1 to 3 $C_{1-4}$alkyl substituents, $R^3$ is a naphythyl, indolyl, benzothienyl, benzofuranyl, benzothiazolyl, quinolinyl or isoquinolinyl group, said group being optionally substituted, and n is 1 or 2; or a salt or ester thereof.

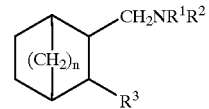

(I)

16 Claims, No Drawings

3-BICYCLOARYL-2-AMINOMETHYL BICYCLOALKANES AS SEROTONINE REUPTAKE INHIBITORS

This application is a 371 of PCT/GB00/01294 filed Apr. 4, 2000.

This invention relates to novel compounds having pharmaceutical properties.

Certain aminoalkyl bicycloheptanes having a pharmacological effect on the central nervous system, are disclosed in British Patent 1 586 249. Also, British Patents 1 444 717 and 1 549 174 describe aminoalkyl bicyclooctyl derivatives with similar properties.

The compounds of the invention are of the following formula:

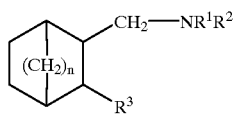
(I)

in which $R^1$ and $R^2$ are each hydrogen or $C_{1-4}$ alkyl, or
  $R^1$ and $R^2$ together with the nitrogen atom to which they are attached form an azetidinyl, pyrrolidinyl, piperidinyl, piperazinyl or morpholino group, said group being optionally substituted with 1 to 3 $C_{1-4}$ alkyl substituents,
  $R^3$ is a naphthyl, indolyl, benzothienyl, benzofuranyl, benzothiazolyl, quinolinyl or isoquinolinyl group, said group being optionally substituted, and n is 1 or 2;
  or a salt or ester thereof.

The compounds of the invention and their pharmaceutically acceptable salts and esters are indicated for use in the treatment of disorders of the central nervous system.

In the above formula (I), $R^1$ and $R^2$ are preferably hydrogen or $C_{1-4}$ alkyl.

A $C_{1-4}$ alkyl group can be methyl, ethyl, or propyl, and can be branched or unbranched and includes isopropyl and tert. butyl. Preferably $R^1$ and $R^2$ are each hydrogen, methyl or ethyl, and especially hydrogen or methyl. The —$NR^1R^2$ group is most preferably —$N(CH_3)_2$ or —$NH(CH_3)$.

Compounds of formula (I) are preferably bicycloheptyl derivatives (n is 1).

The $R^3$ substituent is attached to the bicyclo ring at certain positions on the substituent, and examples of $R^3$ groups are a-naphthyl, β-naphthyl, 2-, 3-, 5- or 6-indolyl, 2-, 3-, 5- or 6-benzothienyl, 2-, 3-, 5- or 6-benzofuranyl, 2- or 5-benzothiazolyl, 2-, 3-, 6- or 7-quinolinyl or 3-, 6- or 7-isoquinolinyl. A naphthyl group is preferably β-naphthyl. Preferred $R^3$ substituents are β-naphthyl, 2-, 3-, 5- or 6-indolyl, 2-, 3-, 5- or 6-benzothienyl and 2-, 3-, 5- or 6-benzofuranyl.

The $R^3$ group can also be substituted, substitution being in one or both rings, with one or more, preferably 1 to 3, substituents. Preferred substituents include $C_{1-4}$ alkyl, $C_{1-4}$ alkoxy, carboxy, hydroxy, cyano, halo, trifluoromethyl, —NR'R" and —CONR'R" where R' and R" are each hydrogen or $C_{1-4}$ alkyl.

A preferred value of $R^3$ is optionally substituted β-naphthyl, and especially unsubstituted β-naphthyl.

A further preferred value of $R^3$ is optionally substituted 2-, 3-,5- or 6-benzothienyl.

As indicated above, it is possible to prepare salts of the compound of the invention and such salts are included in the invention. Such salts are preferably the pharmaceutically acceptable, non-toxic salts. Of special interest are acid addition salts, in particular those with suitable acids, such as those with inorganic acids, for example hydrochloric, hydrobromic, nitric, sulphuric or phosphoric acids, or with organic acids, such as organic carboxylic acids, for example, maleic, fumaric, tartaric or citric acid.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

It will be appreciated that when a substituent on an $R^3$ group is acidic such as, for example, a carboxy group, the opportunity exists for esters. These can be aliphatic or aromatic, being preferably alkyl esters derived from $C_{1-4}$ alkanols, especially methyl and ethyl esters. An example of an ester substituent is —COOR' where R' is $C_{1-4}$ alkyl.

The compounds of the invention contain asymmetric carbon atoms as indicated by asterisks in the following structures:

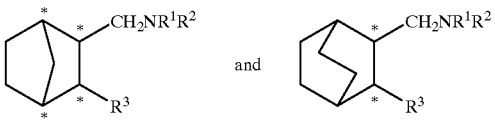

This asymmetry gives rise to cis- and trans-isomers as well as, in the case of the bicycloheptyl derivatives, exo- and endo-forms. Thus the bicycloheptyl derivatives exist as trans exo, trans endo, cis exo and cis endo forms, and in each instance R and S enantiomers. In the case of the bicyclooctyl derivatives, there are cis and trans derivatives only, each of which exist in R and S enantiomeric form. The compounds can be prepared as racemic mixtures and can conveniently be used a such, but individual isomers can be isolated by conventional techniques, or are preferably prepared by chiro-selective methods. Both racemic mixtures and individual isomers are included in the present invention.

A preferred group of compounds of formula (I) above is one in which $R^1$ and $R^2$ are each hydrogen or $C_{1-4}$ alkyl, and $R^3$ is optionally substituted β-naphthyl.

A further preferred group of compounds of formula (I) is one in which $R^1$ and $R^2$ are each hydrogen or $C_{1-4}$ alkyl, and $R^3$ is optionally substituted benzothienyl.

A preferred group of compounds of the invention can be represented as follows:

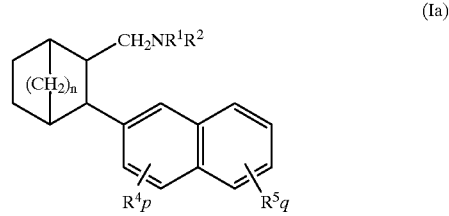
(Ia)

in which $R^1$ and $R^2$ are each hydrogen or $C_{1-4}$ alkyl, $R^4$ and $R^5$ are each $C_{1-4}$ alkyl, $C_{1-4}$ alkoxy, carboxy, hydroxy, cyano, halo, trifluoromethyl, —NR'R" or —CONR'R", where R' and R" are each hydrogen or $C_{1-4}$ alkyl, and p and q are each 0 or 1 to 3, such that the sum of p and q is preferably 0 or 1 to 3; or a salt thereof. When the naphthyl group is substituted there is preferably a single substituent at the 6-position. Of the above compounds of formula (Ia), the most preferred are the unsubstituted compounds in which p and q are both 0, and furthermore the compounds in which n is 1, the bicycloheptyl derivatives, are most preferred.

A further preferred group of compounds of the invention can be represented as follows:

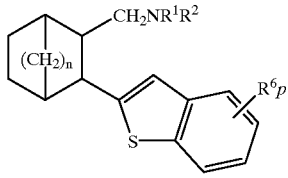

(Ib)

in which $R^1$ and $R^2$ are each hydrogen or $C_{1-4}$ alkyl, and $R^6$ is $C_{1-4}$ alkyl, $C_{1-4}$ alkoxy, carboxy, hydroxy, cyano, halo, trifluoromethyl, —NR'R" or —CONR'R", where R' and R" are each hydrogen or $C_{1-4}$ alkyl, and p is 0 or 1 to 3; or a salt thereof. When p is 2 or 3, the substituents can be different.

A further preferred group of compounds of the invention can be represented as follows:

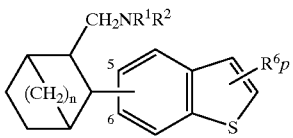

(Ic)

where the bicyclo group is attached at the 5- or 6-position, and in which $R^1$ and $R^2$ are each hydrogen or $C_{1-4}$ alkyl, and $R^6$ is $C_{1-4}$ alkyl, $C_{1-4}$ alkoxy, carboxy, hydroxy, cyano, halo, trifluoromethyl, —NRR'R" or —CONR'R", where R' and R" are each hydrogen or $C_{1-4}$ alkyl, and p is 0, 1 or 2; or a salt thereof. When p is 2, the substituents can be different.

As examples of compounds of the invention, and their pharmaceutically acceptable salts, in isomeric or racemic form, there are included:

N,N-Dimethyl(3-naphthalen-2-ylbicyclo[2.2.1]hept-2-yl)methanamine
N-Methyl(3-naphthalen-2-ylbicyclo[2.2.1]hept-2-yl)methanamine
[(3-(6-Methoxy-2-naphthyl)bicyclo[2.2.1]hept-2-yl]-N,N-dimethylmethanamine
[3-(1-Benzothien-3-yl)bicyclo[2.2.1]hept-2-yl]-N,N-dimethylmethanamine
[3-(1-Benzothien-5-yl)bicyclo[2.2.1]hept-2-yl]-N,N-dimethylmethanamine
[3-(1H-Indol-5-yl)bicyclo[2.2.1]hept-2-yl]-N,N-dimethylmethanamine
[3-(6-Fluoro-1-benzothien-2-yl)bicyclo[2.2.1]hept-2-yl]-N,N-dimethylmethanamine
[3-(6-Fluoro-2-naphthylbicyclo[2.2.1]hept-2-yl]-N,N-dimethylmethanamine
[3-(1-Benzothien-7-yl)bicyclo[2.2.1]hept-2-yl]-N,N-dimethylmethanamnine
[3-(1-Benzothien-4-yl)bicyclo[2.2.1]hept-2-yl]-N,N-dimethylmethanamine
[3-(1-Benzothien-6-yl)bicyclo[2.2.1]hept-2-yl]-N,N-dimethylmethanamine
[3-(3-Methoxy-1-benzothien-5-yl)bicyclo[2.2.1]hept-2-yl]-N,N-dimethylmethanamine
[3-(6-Fluoro-1-benzothien-3-yl)bicyclo[2.2.1]hept-2-yl]-N,N-dimethylmethanamine
N,N-Dimethyl-[3-(2-methyl-1-benzothien-5-yl)bicyclo[2.2.1]hept-2-yl]methanamine
N,N-Dimethyl-[3-(3-methyl-1-benzothien-5-yl)bicyclo[2.2.1]hept-2-yl]methanamine
[3-(2-Ethyl-1-benzothien-5-yl)bicyclo[2.2.1]hept-2-yl]-N,N-dimethylmethanamine
[3-(2-Fluoro-1-benzothien-5-yl)bicyclo[2.2.1]hept-2-yl]-N,N-dimethylmethanamine
[3-(3-Bromo-1-benzothien-5-yl)bicyclo[2.2.1]hept-2-yl]-N,N-dimethylmethanamine
[3-(2,3-Dibromo-1-benzothien-5-yl)bicyclo[2.2.1]hept-2-yl]-N,N-dimethylmethanamine
[3-(6-Methoxy-2-naphthyl)bicyclo[2.2.1]hept-2-yl]-N-methylmethanamine
[3-(1-Benzothien-3-yl)bicyclo[2.2.1]hept-2-yl]-N-methylmethanamine
[3-(1-Benzothien-5-yl)bicyclo[2.2.1]hept-2-yl]-N-methylmethanamine
[3-(6-Fluoro-1-benzothien-2-yl)bicyclo[2.2.1]hept-2-yl]-N-methylmethanamine
[3-(6-Fluoro-2-naphthyl) bicyclo[2.2.1]hept-2-yl]-N-methylmethanamine
N-Methyl-[3-(3-methyl-1-benzothien-5-yl)bicyclo[2.2.1]hept-2-yl]methanamine
1-{[3-(3-Methoxy-1-benzothien-5-yl)bicyclo[2.2.1]hept-2-yl]methyl}pyrrolidine
1-{[3-(6-Fluoro-1-benzothien-2-yl)bicyclo[2.2.1]hept-2-yl]methyl}pyrrolidine
1-{[3-(3-Methyl-1-benzothien-5-yl)bicyclo[2.2.1]hept-2-yl]methyl}pyrrolidine
6-{[3-[(Dimethylamino)methyl]bicyclo[2.2.1]hept-2-yl}-2-naphthol
(3-Naphthalen-2-ylbicyclo[2.2.2]oct-2-yl)methanamine
[3-(6-Methoxy-2-naphthyl)bicyclo[2.2.2]oct-2-yl]-N,N-dimethylmethanamine
[3-(1H-Indol-3-yl)bicyclo[2.2.2]oct-2-yl]-N,N-dimethylmethanamine
N,N-dimethyl-[3-(2-naphthyl)bicyclo[2.2.2]oct-2-yl]methanamine
[3-(1-Benzothien-5-yl)bicyclo[2.2–2]oct-2-yl]-N,N-dimethylmethanamine
[3-(1H-indol-5-yl)bicyclo[2.2.2]oct-2-yl]-N,N-dimethylmethanamine
N-methyl-[3-(2-naphthyl)bicyclo[2.2.2]oct-2-yl]methanamine The invention also includes processes for the production of compounds of the formula (I) above by any of the well known methods for preparing substituted alkyl amines. For example, they can be made from intermediates of the formula:

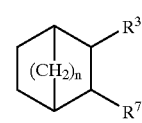

(II)

where $R^3$ and n have the values given above, and $R^7$ is —CN, —CONR$^1$R$^2$, —CH$_2$NCO, —CHO or —COOR$^8$ where $R^8$ is $C_{1-4}$ alkyl.

The compounds of formula (II) are readily converted to compounds of formula (I) by reduction, optionally followed by alkylation. In the case of the nitriles and arnides of formula (II), the reduction is preferably carried out using a complex hydride reducing agent such as lithium aluminium hydride or sodium borohydride, whilst in the case of the isocyanates of formula (II), treatment with a concentrated mineral acid such as hydrochloric acid produces the desired conversion. The aldehydes and esters of formula (II) may be reductively aminated to the desired compounds of formula (I) by reduction to the corresponding alcohols using, for example, a complex hydride reducing agent, conversion of the alcohols to the corresponding alkyl or aryl sulphonates by reaction with an alkyl or aryl sulphonyl chloride such as methyl sulphonyl chloride or p.toluene sulphonyl chloride and reaction of the sulphonates with an amine of formula $HNR_1R_2$. Reductive amination of the aldehydes of formula (II) may also be carried out by catalytic reduction, for example by catalytic hydrogenation in the presence of an amine of formula $HNR_1R_2$.

The compounds are most conveniently prepared from the nitriles and amides of formula (II) and these are the preferred intermediates of the invention. The amides of formula (II) in which $R^7$ is —$CONR^1R^2$ are novel compounds and are included as part of the present invention.

A primary amine produced by the above routes may be converted to a secondary or tertiary amine by alkylation. The alkylation may be carried out in conventional manner, for example by reductive alkylation, reaction with an alkyl halide or sulphate, reaction with an alkyl chloroformate followed by reduction of the resultant urethane, or when methylation is to be carried out, preferably by reaction with formic acidformaldehyde (Eschweiler-Clarke).

Intermediate compounds of formula (II) where $R^7$ is —CN or —CHO can readily be prepared by a Diels-Alder reaction, by the addition of cyclopentadiene or cyclohexadiene to a compound of the formula $R^3CH=CH—CN$ or $R^3CH=CH—CHO$, optionally employing, for example, diethylaluminium chloride as catalyst. The reaction is prolonged and has to be carried out at an elevated temperature, for example, from 100° C. to 200° C., especially about 160° C., yielding bicycloheptenyl or bicyclooctenyl derivatives, which can be catalytically reduced to give the compounds of formula (II), as illustrated below.

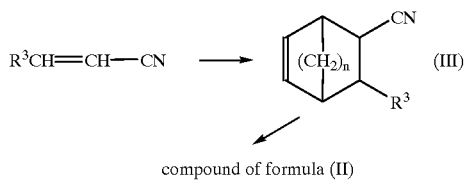

compound of formula (II)

The reaction results in cis- and trans-enantiomers in racemic mixtures, and can be used to produce both the bicycloheptane and bicyclooctane derivatives of formula (I) above.

A reaction which can conveniently be employed to produce chiral enantiomers of the cycloheptyl derivatives utilises Evans chiral auxilliaries as, for example, oxazolidine amide intermediates of the formula:

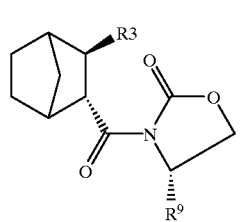

where $R^9$ is alkyl, aryl or aralkyl, from the corresponding a-unsaturated acid, as follows:

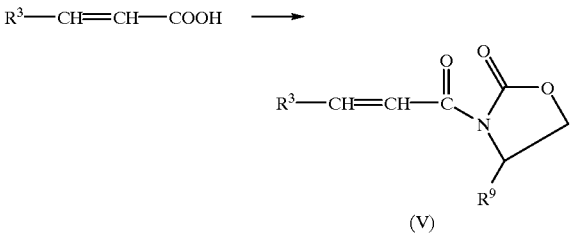

followed by a Diels-Alder reaction with cyclopentadiene in the presence of a Lewis acid and solvent such as dichloromethane, at a low temperature for example between −10° C. and −30° C. The reaction proceeds readily to give a bicycloheptenyl derivative, which on reduction yields the compound of formula (IV) above, as follows:

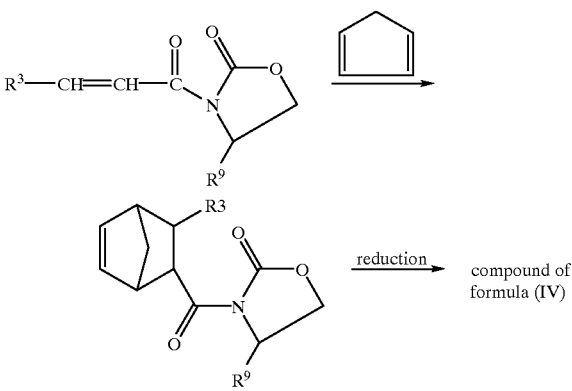

Alternatively, the intermediates of formula (V) can be prepared (1) by reaction of an acryloyloxazolidine with the appropriately saturated $R^3$ leaving species such as an $R^3$ halide, in the presence of PdO, or (2) by reaction of an oxazolidinyl phosphonium halide with the appropriate aldehyde of formula $R^3CHO$ in the presence of a base such as triethylamine.

Alternatively, instead of employing a chiral compound of formula (IV), an oxazolidine compound in which $R^9$ is hydrogen can be used, together with a chiral catalyst.

The compound of formula (IV) is readily converted by action of lithium hydroxide and hydrogen peroxide to the free acid, which on reaction with amine and further reduction yields a compound of formula (I), as follows.

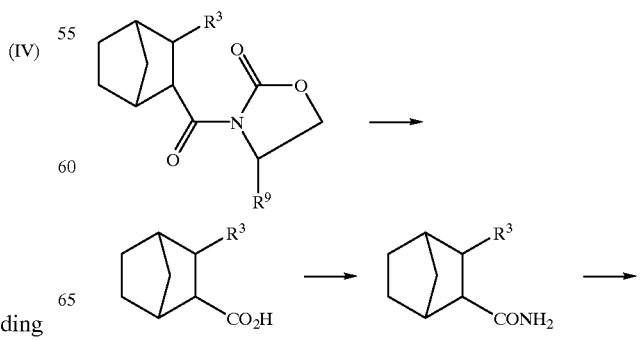

-continued

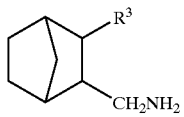

Choice of the appropriate α-unsaturated acid starting material allows the production of enantiomerically pure cis- and trans-isomers.

It will be appreciated that substituents on the naphthyl or heterocyclyl ring can be introduced at the outset, or in the final stages of the synthesis. Sometimes it will be convenient to convert one substituent to another as, for example, $C_{1-4}$ alkoxy to hydroxy, at an intermediate stage or in the final product.

As mentioned above, the compounds of the invention and their pharmaceutically acceptable salts have useful central nervous system activity. The compounds inhibit the uptake of neurotransmitters such as serotonin, dopamine and noradrenalin. They are surprisingly effective serotonin reuptake inhibitors, as evidenced by their displacement of [$^3$H] citalopram at the binding sites on membranes derived from rat cortex, as in the test described below (see Example 23). In a similar test, also employing rat cortex membrane, the compounds displaced nisoxetine, demonstrating their ability to inhibit noradrenalin reuptake, see Journal of Pharmacology and Experimental Therapeutics Vol. 272, No. 3, 1176–1186, 1995. The dopamine reuptake properties of the compounds of the invention are demonstrated in the test described in Molecular Pharmacology 45: 125–135, using membranes derived from rat striatum. In this test displacement of WIN 35,428 from its reuptake site, is measured.

Because of their profile of neurotransmitter reuptake properties, the compounds of the present invention are indicated for use in treating a variety of conditions such as depression, obesity, bulimia, alcoholism, pain, hypertension, ageing, senile dementia, Alzheimer's, memory loss, attention-deficit hyperactivity disorder, sexual dysfunction, Parkinsonism, anxiety, chronic fatigue syndrome, panic disorders, obsessive compulsive disorder, schizophrenia, gastrointestinal disorders, headache, cardiovascular disorders, smoking cessation, drug addiction including cocaine abuse, emesis and sleep disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mgkg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or ester thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Examples illustrate the synthesis of the compounds of invention.

EXAMPLE 1

Ethyl (Z)-3-(2-Naphthyl)prop-2-enoate

To a slurry of magnesium chips (0.62 g, 0.026 mol) in THF (200 ml) under $N_2$ was added a solution of 2-bromonaphthalene (5 g, 0.024 mol) in THF (10 ml). The mixture was heated under reflux overnight. on cooling, solid $ZnBr_2$ (3.62 g, 0.016 mol) was added in one portion and the resulting white precipitate left to stir at room temperature for 20 hours. DMF (20 ml) was added, followed by bis (acetonitrile) palladium(II) chloride (0.02 g, 0.8 mmol) and ethyl cis-iodoacrylate (1.03 ml, 8.0 mmol).

After 1 hour, 2N HCl was added, the mixture diluted with diethyl ether and washed with a saturated solution of ammonium chloride. The ethereal phase was dried and the solvent removed in vaccuo. Chromatography on flash silica gel using hexane:dichloromethane (1:1) gave Ethyl (Z)-3-(2-naphthyl)prop-2-enoate as a white solid, M/e 227 (M+H$^+$).

EXAMPLE 2

(Z)-3-(2-Naphthyl)prop-2-enoic Acid

A solution of (Z)-naphthalene-2-acrylic acid ethyl ester (1.38 g, 6.0 mmole) in a mixture of tetrahydrofuran (10 ml) and water (10 ml) was treated with lithium hydroxide (0.88 g, 37 mmol) and heated to 60° C. for 6 hours. On cooling, the organic phase was separated and the. aqueous phase was acidified and extracted with diethyl ether. The ethereal phase was dried and the solvent removed in vaccuo to give (Z)-3-(2-naphthyl)prop-2-enoic acid as a white solid which was used without further purification, Mp 207–209° C.

EXAMPLE 3

3-[(E)-3-Naphthalen-2-ylprop-2-enoyl]-1,3-oxazolidin-2-one

To a stirred solution of (E)-3-(2-naphthyl)prop-2-enoic acid (10 g, 0.05 mole) at −78° C., was added triethylamine (8.42 ml, 0.06 mole) and pivaloyl chloride (7.5 ml, 0.06 mole). Stirring was continued for 1 hour. To a stirred solution of oxazolidinone (5.14 g, 0.06 mole) in dry tetrahydrofuran (200 ml) at −78° C. was added slowly n-butyl lithium (1.6M in hexanes, 38 ml, 0.06 mole). Stirred for 1 hour. The suspension of the mixed anhydride was transferred into the oxazolidinone anion by means of a canula maintaining the temperature below −60° C. The resulting reaction mixture was stirred for 2 hours. Water was added cautiously and the reaction extracted with ethyl acetate. The solvent was washed with brine, dried and evaporated to dryness in-vacuo. Chromatography on flash silica using ethyl acetatehexane (1:1) gave 3-[(E)-3-naphthalen-2-ylprop-2-enoyl]-1,3-oxazolidin-2-one as a white solid, M/e 268 (M+H).

Similarly prepared were:
4(R)-3-[(E)-3-naphthalen-2-ylprop-2-enoyl]-4-benzyl-1,3-oxazolidin-2-one, Mp121–123° C.
4(S)-3-[(E)-3-naphthalen-2-ylprop-2-enoyl]-4-benzyl-1,3-oxazolidin-2-one, Mp121–123° C.
3-[(Z)-3-naphthalen-2-ylprop-2-enoyl]-1,3-oxazolidin-2-one, M/e 268 (M+H$^+$), 290 (M+Na$^+$).
4(R)-3-[(Z)-3-naphthalen-2-ylprop-2-enoyl]-4-benzyl-1,3-oxazolidin-2-one, M/e 358 (M+H$^+$).

EXAMPLE 4

(4R)-3-[(2E)-3-(1-Benzothien-7-yl)-2-propenoyl]-4-benzyl-1,3-oxazolidin-2-one

To a stirred solution of 7-bromobenzothiophene (3.58 g, 16.80 mmol) in dry acetonitrile was added (4R)-3-acryloyl-4-benzyl-1,3-oxazilidin-2-one (4.27 g, 18.48 mmol), followed by tritolylphosphine (1.02 g, 3.36 mmol), palladium acetate (377 mg, 1.68 mmol) and finally triethylamine (4.67 ml, 33.60 mmol). The mixture was heated to reflux for 3 hours. When cool, water was added to quench the reaction. The aqueous phase was extracted with dichloromethane. The organic phase was washed with brine, dried over magnesium sulphate and concentrated in vacuo. Purification was achieved by column chromatography on flash silica, using a mixture of ⅛ of ethyl acetate and hexane as an eluant to give (4R)-3-[(2E)-3-(1-benzothien-7-yl)-2-propenoyl]-4-benzyl-1,3-oxazolidin-2-one as a yellow solid in 60% yield., M/e 364 (MH+).

EXAMPLE 5

3-[(E)-3-Naphthalen-2-ylprop-2-enoyl]-1,3-oxazolidin-2-one

To a stirred solution of 4S-4-(benzyl)-2-oxazolidinone (20 g, 0.113 mol) in dried tetrahydrofuran (200 ml) cooled to −780 under nitrogen was added dropwise a solution of n-butyl lithium 2.5M in hexane (45.2 ml). After 10 min, chloroacetyl chloride (12.76 g) was added dropwise. The resulting solution was stirred at −78° for 15 min then allowed to warm to room temperature. After 15 min a saturated solution of ammonium chloride (100 ml) was added and the mixture concentrated in vacuo. The residue was extracted with diethyl ether, the extracts were washed with aqueous ammonium chloride, dried, filtered and evaporated to give a colourless solid (28.9 g).

A solution of the (4S)-4-benzyl -3-(chloroacetyl)-1,3-oxazolidin-2-one(29.08 g 0.11 mol) and triphenylphosphine (36.1 g, 0.138 mol) in toluene (150 ml) was stirred at room temperature. After 72h a yellow gummy solid of the phosphonium salt precipitated. The mixture was decanted and the gum triturated with toluene and diethyl ether. The residue was dried to a pale yellow solid (46.46 g) of (4S)-4-benzyl-3-[(triphenylphosphino)acetyl]-1,3-oxazolidin-one chloride.

A mixture of (4S)-4-benzyl-3-[(triphenylphosphino)acetyl]-1,3-oxazolidin-one chloride (10 mg, 0.193 mmol), 2-naphthaldehyde (30 mg, 0.193 mmol), triethylamine (0.030 ml, 0.212 mmol) and 4-(dimethylamino)pyridine in acetonitrile (5 ml) was heated under reflux for 24 h. After evaporation, the residue was dissolved in hexaneether-dichloromethane and chromatographed on flash silica eluting with hexane:ether 3:2 to give a white solid (36 mg, 52%) of 3-[(E)-3-Naphthalen-2-ylprop-2-enoyl]-1,3-oxazolidin-2-one. M/e 358 (MH+).

EXAMPLE 6 trans-endo-3-[(3-Naphthalen-2-ylbicyclo[2.2.1]hept-5-en-2-yl)carbonyl]-1,3-oxazolidin-2-one and Trans-exo-3-[( 3-naphthalen-2-ylbicyclo[2.2.1]hept-5-en-2-yl)carbonyl]-1,3-oxazolidin-2-one To a solution of 3-[(E)-3-naphthalen-2-ylprop-2-enoyl]-1,3-oxazolidin-2-one (2 g, 7.5 mmole) in dry dichloromethane (20 ml) at −20° C. was added freshly cracked cyclopentadiene (3.2 g, 37 mmole) and diethylaluminium chloride (5.4 ml, 9.7 mmole). The reaction mixture was stirred for 2 hours. The reaction was poured into ice water and the solvent separated. The aqueous was extracted with dichloromethane and the combined solvent washed with brine, dried and evaporated to dryness in-vacuo. Chromatography on flash silica using ethyl acetatehexane (3:7)gave trans-endo-3-[(3-naphthalen-2-ylbicyclo[2.2.1]hept-5-en-2-yl)carbonyl]-1,3-oxazolidin-2-one, M/e 334 (M+H$^+$), and trans-exo-3-[(3-naphthalen-2-ylbicyclo[2.2.1]hept-5-en-2-yl)carbonyl]-1,3-oxazolidin-2-one, M/e 334 (M+H$^+$).

Similarly prepared were:
trans-endo-4(R)-3-[(3-naphthalen-2-ylbicyclo[2.2.1]hept-5-en-2-yl)carbonyl]-4-benzyl-1,3-oxazolidin-2-one, Mp135–136° C.
trans-endo-4 (S)-3-[(3-naphthalen-2-ylbicyclo[2.2.1]hept-5-en-2-yl)carbonyl]-4-benzyl-1,3-oxazolidin-2-one, Mp135–136° C.
cis-endo-3-[(3-naphthalen-2-ylbicyclo[2.2.1]hept-5-en-2-yl)carbonyl]-1,3-oxazolidin-2-one, Mp194–196° C.
cis-exo-3-[(3-naphthalen-2-ylbicyclo[2.2.1]hept-5-en-2-yl) carbonyl)-1,3-oxazolidin-2-one

EXAMPLE 7 trans-endo-3-[(3-Naphthalen-2-ylbicyclo[2.2.1]hept-5-en-2-yl)carbonyl]-1,3-oxazolidin-2-one A solution of the catalyst was prepared under nitrogen by stirring together anhydrous copper(ll)chloride (0.0046 g, 0.034×10$^{-3}$ mol), 2,2'-isopropylidenebis(4-S)-4-tert-butyl-2-oxazoline (0.012 g, 0.038×10$^{-3}$ mol) and silver(ll) hexafluoroantimonate (0.024 g, 0.068×10$^{-3}$ mol) in dry dichloromethane (0.34 ml) at room temperature for 8 hours. The solid precipitate was removed by filtration through a celite pad and the bright blue catalyst solution was added under nitrogen to a stirred slurry of 3-[(E)-3-naphthalen-2-ylprop-2-enoyl]- 1,3-oxazolidin-2-one (0.05 g, 0.0019 mol) in dry dichloromethane (1 ml). Freshly cracked cyclopentadiene (0.2 ml, 0.0023 mol) was added and the mixture stirred at room temperature for 24 hours. After this time, the solvent was removed in vacuo and the residue purified by column chromatography, eluent 7:3 hexane:ethyl acetate, to give trans-endo-3-[(3-naphthalen-2-ylbicyclo[2.2.1]hept-5-en-2-yl)carbonyl]-1,3-oxazolidin-2-one as a white solid. Mp 135–136° C.

EXAMPLE 8 trans-endo-3-[(3-Naphthalen-2-ylbicyclo[2.2.1]hept-2-yl)carbonyl]-1,3-oxazolidin-2-one To a solution of trans-endo-3-[(3-naphthalen-2-ylbicyclo[2.2.1]hept-5-en-2-yl)carbonyl]-1,3-oxazolidin-2-one (1 g, 3 mmole) in ethyl acetate (20 ml) was added 10%Pd—C (0.1 g). The reaction was hydrogenated at 60 psi using a Parr hydrogenator for 1 hour. The catalyst was removed by filtration through celite and the solvent removed by evaporation in-vacuo. The product was purified by chromatography on flash silica using ethyl acetatehexane (3:7) to give trans-endo-3-[(3-naphthalen-2-ylbicyclo[2.2.1]hept-2-yl) carbonyl]-1,3-oxazolidin-2-one as a colourless oil, M/e 336 (M+H$^+$).

Similarly prepared were:

trans-exo-3-[(3-naphthalen-2-ylbicyclo[2.2.1]hept-2-yl)carbonyl]-1,3-oxazolidin-2-one, M/e 336 (M+H$^+$).

trans-endo-4 (R)-3-[(3-naphthalen-2-ylbicyclo[2.2.1]hept-2-yl)carbonyl]-4-benzyl-1,3-oxazolidin-2-one, Mp141–143° C.

trans-endo-4 (S)-3-[(3-naphthalen-2-ylbicyclo[2.2.1]hept-2-yl)carbonyl]-4-benzyl-1,3-oxazolidin-2-one, Mp141–143° C.

cis-endo-3-[(3-naphthalen-2-ylbicyclo[2.2.1]hept-2-yl)carbonyl]-1,3-oxazolidin-2-one.

cis-exo-3-[(3-naphthalen-2-ylbicyclo[2.2 .1]hept-2-yl)carbonyl]-1,3-oxazolidin-2-one.

EXAMPLE 9 trans-endo-3-Naphthalen-2-ylbicyclo[2.2.1]heptane-2-carboxylic Acid

To a solution of trans-endo-3-[(3-naphthalen-2-ylbicyclo[2.2.1]hept-2-yl)carbonyl]-1,3-oxazolidin-2-one (0.29 g, 0.86 mmole) in a mixture of tetrahydrofuran (20 ml) and water (5 ml) at –5° C. was added hydrogen peroxide (2 ml) dropwise. To the resulting slurry was added a solution of lithium hydroxide (42 mg, 0.18mmole) in water (5 ml) dropwise, keeping the temperature below 0° C. The resulting mixture was stirred 1 hour at 0° C. and then for 2 hours at room temperature. The reaction was quenched with a solution of sodium sulphide in water made acid with 6NHCl and extracted with dichloromethane. The solvent was washed with brine, dried and evaporated to dryness in-vacuo. Chromatography on flash silica using ethyl acetate:hexane (1:1) gave trans-endo-3-naphthalen-2-ylbicyclo[2.2.1]heptane-2-carboxylic acid, M/e 267 (M+H$^+$).

Similarly prepared were:

trans-exo-3-naphthalen-2-ylbicyclo[2.2.1]heptane-2-carboxylic acid, M/e 267 (M+H$^+$).

trans-endo-(2R,3R)-3-naphthalen-2-ylbicyclo[2.2.1] heptane-2-carboxylic acid, Mp135–137° C.

trans-endo-(2S,3S)-3-naphthalen-2-ylbicyclo[2.2.1] heptane-2-carboxylic acid, Mp135–137° C.

cis-endo-3-naphthalen-2-ylbicyclo[2.2.1]heptane-2-carboxylic acid.

cis-exo-3-naphthalen-2-ylbicyclo[2.2.1]heptane-2-carboxylic acid.

EXAMPLE 10 trans-endo-N, N-Dimethyl-3-naphthalen-2-ylbicyclo [2.2.1]heptane-2-carboxamide

To a stirred solution of trans-endo-3-naphthalen-2-ylbicyclo[2.2.1]heptane-2-carboxylic acid (225 mg) in dichloromethane (5 ml) at 0–5° C. was added oxalyl chloride (81 µl, 0.93 mmole) followed by dry dimethylformamide (1 drop). The mixture was allowed to attain room temperature and stirred for 2 hours. The solution was evaporated to dryness in-vacuo, re-dissolved in dry tetrahydrofuran and added to a stirred solution of dimethylamine in tetrahydrofuran (2M solution, 0.9 ml, 1.7 mmole). The mixture was stirred for 2-hours. The reaction mixture was diluted with ice-water, extracted with ethyl acetate, washed with water, dried and evaporated to dryness in-vacuo. Chromatography on flash silica using ethyl acetate:hexane (1:1) gave trans-endo-N,N-dimethyl-3-naphthalen-2-ylbicyclo[2.2.1] heptane-2-carboxamide as a colourless oil, M/e 294 (M+H$^+$).

Similarly prepared were:

trans-exo-N,N-dimethyl-3-naphthalen-2-ylbicyclo[2.2.1] heptane-2-carboxamide, M/e 294 (M+H$^+$).

trans-endo-(2R,3R)-N,N-dimethyl-3-naphthalen-2-ylbicyclo[2.2.1]heptane-2-carboxamide, Mp140 –142° C.

trans-endo-(2S,3S)-N,N-dimethyl-3-naphthalen-2-ylbicyclo [2.2.1]heptane-2-carboxamide, Mp140 –142° C.

trans-endo-N-methyl-3-naphthalen-2-ylbicyclo[2.2.1] heptane-2-carboxamide.

trans-endo-(2R,3R)-N-methyl-3-naphthalen-2-ylbicyclo [2.2.1]heptane-2-carboxamide.

trans-endo-(2S,3S)-N-methyl-3-naphthalen-2-ylbicyclo [2.2.1]heptane-2-carboxamide, M/e 280 (M+H$^+$).

cis-endo-N,N-dimethyl-3-naphthalen-2-ylbicyclo[2.2.1] heptane-2-carboxamide.

cis-exo-N,N-dimethyl-3-naphthalen-2-ylbicyclo[2.2.1] heptane-2-carboxamide.

EXAMPLE 11

(1S,2R,3S,4R)-3-(2-methyl-1-benzothien-5-yl)-N,N-dimethylbicyclo[2,2,1]heptane-2-carboxamide.

To a stirred solution of (1S,2R,3S,4R)-3-(1-benzothien-5-yl)-N,N-dimethylbicyclo[2,2,1]heptane-2-carboxamide (200 mg, 0.67 mmol) in dry tetrahydrofuran (5 mL) at −78° C. was added lithium diisopropylamide (1.67 mL, 3.35 mmol). The mixture was stirred at this temperature for 1 hour before iodomethane (2.3 mL, 3.35 mmol) was added. The mixture was stirred for another 10 minutes at this temperature before it was allowed to warm to room temperature. After 1 hour, water was added and the layers were separated. The aqueous phase was extracted with ethyl acetate (2×10 mL) and the extracts were washed with water (2×10 mL) dried over magnesium sulphate and evaporated in-vacuo. Column chromatography with 20% ethyl acetate in hexane provided the (1S,2R,3S,4R)-3-(2-methyl-1-benzothien-5-yl)-N,N-dimethylbicyclo [2,2,1]heptane-2-carboxamide as a glass (140 mg, 66%). M/e 314 (M+H$^+$).

Similarly prepared was:

(1S,2R,3S,4R)-3-(2-ethyl-1-benzothien-5-yl)-N,N-dimethylbicyclo[2,2,1]heptane-2-carboxamide, M/e 328 (MH+).

EXAMPLE 12

(1S,2R,3S,4R)-3-(2-Fluoro-1-benzothien-5-yl)-N,N-dimethylbicyclo [2,2,1]heptane-2-carboxamide To a stirred solution of (1S,2R,3S,4R)-3-(1-benzothien-5-yl)-N,N-dimethylbicyclo [2,2,1]heptane-2-carboxamide (200 mg, 0.67 mmol) in dry tetrahydrofuran (5 mL) at −78° C. was added lithium diisopropylamide (1.67 mL, 3.35 mmol). The mixture was stirred at this temperature for 1 hour before N-fluorobenzene sulfonimide (2.3 mL, 3.35 mmol) was added. The mixture was stirred for another 10 minutes at this temperature before it was allowed to warm to room temperature. After 1 hour, water was added and the layers were separated. The aqueous phase was extracted with ethyl acetate (2×10 mL) and the extracts were washed with water (2×10 mL) dried over magnesium sulphate and evaporated in-vacuo. Column chromatography with 20% ethyl acetate in hexane provided (1S,2R,3S,4R)-3-(2-fluoro-1-benzothien-5-yl)-N,N-dimethylbicyclo[2,2,1]heptane-2-carboxamide.

mp 159–161 C.

EXAMPLE 13

(1S,2R,3S,4R)-3-(3-Bromo-1-benzothien-5-yl)-N,N-dimethylbicyclo[2,2,1]heptane-2-carboxamide To a solution of (1S,2R,3S,4R)-3-(1-benzothien-5-yl)-N,N-dimethylbicyclo[2,2,1]heptane-2-carboxamide (30 mg, 0.1 mmol) in acetic acid (2 mL) was added bromine (5.5 µL, 0.1 mmol) and the mixture was stirred at room temperature for 16 hours. The mixture was diluted with methylene chloride (5 mL) and neutralised by careful addition of a saturated hydrogen carbonate solution. The layers were separated and the aqueous was extracted with methylene chloride (2×5 mL). The organic extracts were washed with water, dried over magnesium sulfate and evaporated in vacuo to give (1S,2R,3S,4R)-3-(3-bromo-1-benzothien-5-yl)-N,N-dimethylbicyclo[2,2,1]heptane-2-carboxamide as a glass (37 mg, 97%). M/e 378/380 (MH$^+$).

Similarly prepared was:

(1S,2R,3S,4R)-3-(2,3-dibromo-1-benzothien-5-yl)-N,N-dimethylbicyclo[2,2,1]heptane-2-carboxamide, M/e 466/468/470 (MH+).

EXAMPLE 14 trans-endo-N,N-Dimethyl(3-naphthalen-2-ylbicyclo [2.2.1]hept-2-yl)methanamine

To a stirred solution of trans-endo-N,N-dimethyl-3-naphthalen-2-ylbicyclo[2.2.1]heptane-2-carboxamide (0.45 g, 1.53 mmole) in dry ether (20 ml) was added a solution of lithium aluminium hydride in tetrahydrofuran (2M, 0.84 ml, 1.7 mmole). The reaction was heated at reflux for 1 hour. After cooling to room temperature water (1 ml) was added dropwise with caution followed by 2NNaOH (1 ml). When gas evolution ceased the reaction mixture was filtered through a pad of celite which was well washed with ether. The ether solution was dried and after removal of the solvent in-vacuo the product was converted to the hydrochloride salt and re-crystallised from ethanolether to give trans-endo-N,N-dimethyl(3-naphthalen-2-ylbicyclo[2.2.1]hept-2-yl)methanamine, Mp 249–250° C.

Similarly prepared, as hydrochloride or maleate salts, were:

trans-exo-N,N-dimethyl(3-naphthalen-2-ylbicyclo[2.2.1] hept-2-yl)methanamine, M/e 280 (M+H$^+$).

trans-endo-N,N-dimethyl[(2R,3R)-3-naphthalen-2-ylbicyclo[2.2.1]hept-2-yl]methanamine, α$_D$–44.4 (c 0.5, MeOH, 25° C.).

trans-endo-N,N-dimethyl](2S,3S)-3-naphthalen-2-ylbicyclo [2.2.1]hept-2-yl]methanamine, α$_D$+44.4 (c 0.5, M/eOH, 25° C.).

trans-endo-N-methyl (3-naphthalen-2-ylbicyclo [2.2.1]hept-2-yl)methanamine.

trans-endo-N-methyl[(2R,3R)-3-naphthalen-2-ylbicyclo [2.2.1]hept-2-yl ]methanamine.

trans-endo-N-methyl[(2S,3S)-3-naphthalen-2-ylbicyclo [2.2.1]hept-2-yl]methanamine, mp=210–212° C.

cis-N,N-dimethyl (3-naphthalen-2-ylbicyclo[2.2.1]hept-2-yl)methanamine, mp255–257° C.

N,N-dimethyl[(2R,3R)-3-(1-naphthyl)bicyclo[2.2.1]hept-2-yl]methanamine, M/e 280 (MH+).

[(1S,2S,3S,4R)-3-(6-methoxy-2-naphthyl)bicyclo[2.2.1] hept-2-yl]-N,N-dimethylmethanamine, mp=145–146 C.

[(1S,2S,3S,4R)-3-(1-benzothien-3-yl)bicyclo[2.2.1]hept-2-yl]-N,N-dimethylmethanamine, mp=208–210 C.

[(1S,2S,3S,4R)-3-(1-benzothien-5-yl)bicyclo[2.2.1]hept-2-yl]-N,N-dimethylmethanamine, mp=145–146 C.

[(1S,2S,3S,4R)-3-(1H-indol-5-yl)bicyclo[2.2.1]hept-2-yl]-N,N-dimethylmethanamine, mp=148–149 C.

[(1S,2S,3S,4R)-3-(6-fluoro-1-benzothien-2-yl)bicyclo [2.2.1]hept-2-yl)-N,N-dimethylmethanamine, M/e 304 (MH+).

[(1S,2S,3S,4R)-3-(6-fluoro-2-naphthyl)bicyclo[2.2.1]hept-2-yl]-N,N-dimethylmethanamine, mp=137–138 C.

[(1S,2S,3S,4R)-3-(1-benzothien-7-yl)bicyclo[2.2. 1]hept-2-yl]-N,N-dimethylmethanamine, M/e 286 (MH+).

[(1S,2S,3S,4R)-3-(1-benzothien-4-yl)bicyclo[2.2.1]hept-2-yl]-N,N-dimethylmethanamine, mp=114–116 C.

[(1S,2S3S,4R)-3-(1-benzothien-6-yl)bicyclo[2.2.1]hept-2-yl]-N,N-dimethylmethanamine, mp=240–242 C.

[(1S,2S,3S,4R)-3-(3-methoxy-1-benzothien-5-yl)bicyclo [2.2.1]hept-2-yl]-N,N-dimethylmethanamine, mp=154–156 C.

[(1S,2S,3S,4R)-3-(6-fluoro-1-benzothien-3-yl)bicyclo [2.2.1]hept-2-yl]-N,N-dimethylmethanamine, M/e 304 (MH+).

N,N-dimethyl[(1R,2R,3R,4S)-3-(3-methyl-1-benzothien-5-yl)bicyclo[2.2.1]hept-2-yl]methanamine, mp=250–252 C.

N,N-dimethyl[(1S,2S,3S,4R)-3-(2-methyl-1-benzothien-5-yl)bicyclo[2.2.1]hept-2-yl]methanamine, mp=192–194 C.

[(1S,2S,3S,4R)-3-(2-ethyl-1-benzothien-5-yl)bicyclo[2.2.1] hept-2-yl]-N,N-dimethylmethanamine, mp=167–169 C.

[(1S,2S,3S,4R)-3-(2-fluoro-1-benzothien-5-yl)bicyclo [2.2.1]hept-2-yl]-N,N-dimethylmethanamine, mp=159–161 C.

[(1S,2S,3S,4R)-3-(3-bromo-1-benzothien-5-yl)bicyclo [2.2.1]hept-2-yl]-N,N-dimethylmethanamine, M/e 346366 (MH+).

[(1S,2S.3S,4R)-3-(2,3-dibromo-1-benzothien-5-yl)bicyclo [2.2.1]hept-2-yl]-N,N-dimethylmethanamine, mp=101–107 C.

[(1R,2R,3R,4S)-3-(6-methoxy-2-naphthyl)bicyclo [2.2.1] hept-2-yl]-N-methylmethanamine, mp=208–210 C.

[(1S,2S,3S,4R)-3-(1-benzothien-3-yl)bicyclo[2.2.1]hept-2-yl]-N-methylmethanamine, M/e 272 (MH+).

[(1S,2S,3S,4R)-3-(1-benzothien-5-yl)bicyclo[2.2.1]hept-2-yl]-N-methylmethanamine, mp=165–162 C.

[(1S, 2S, 3S, 4R)-3-(6-fluoro-1-benzothien-2-yl)bicyclo (2.2.1]hept-2-yl]-N-methylmethanamine, M/e 290 (MH+).

[(1S,2S,3S,4R)-3-(6-fluoro-2-naphthyl)bicyclo[2.2.1]hept-2-yl]-N-methylmethanamine, mp=167–169 C.

N-methyl [(1R,2R,3R,4S)-3-(3-methyl-1-benzothien-5-yl) bicyclo[2.2.1]hept-2-yl]methanamine, mp=260–262 C.

1-{[(1S,2S,3S,4R)-3-(3-methoxy-1-benzothien-5-yl)bicyclo [2.2.1]hept-2-yl]methyl}pyrrolidine, mp=124–126 C.

1-{[(1S,2S,3S,4R)-3-(6-fluoro-1-benzothien-2-yl) bicyclo [2.2.1]hept-2-yl]methyl}pyrrolidine, M/e 330 (MH+).

1-{[(1R,2R,3R,4S)-3-(3-methyl-1-benzothien-5-yl)bicyclo [2.2.1]hept-2-yl]methyl}pyrrolidine, 198–200 C.

EXAMPLE 15

6-{(1R,2S,3S,4S)-3-[(Dimethylamino)methyl] bicyclo[2.2.1]hept-2-yl}-2-naphthol

To a stirred solution of [(1S,2S,3S,4R)-3-(6-methoxy-2-naphthyl)bicyclo [2.2.1]hept-2-yl]-N, N-dimethyl methanamine in DMF was added sodium ethane thionyl. The mixture was heated to 100 C for 40 hours. When cool, water was added to quench the reaction. The aqueous phase was extracted with ethyl acetate. The organic phase was washed with water, brine, dried over magnesium sulfate and concentrated in-vacuo. Purification was achieved by column chromatography, using flask silica and DCMM/eOH(M/eOH,NH40H at 10%) in a ration of 10/1/0.1 for eluant. Yield (10%). ME 296 (MH+).

EXAMPLE 16 trans-3-Naphthalen-2-ylbicyclo [2.2.2]oct-5-ene-2-carbonitrile

A mixture of (E)-(2-naphthyl)-acrylonitrile (1.8 g, 0.01 mole) and 1,3-cyclohexadiene (8 g, 0.1 mole) in 1,2-dichlorobenzene (10 ml) was placed in a teflon lined stainless steel bomb and heated at 180° C. for 3 days. The vessel was allowed to cool to room temperature and the contents transferred to a Buchi flask. The solvent was removed under high vacuum and the product purified by chromatography on flash silica by elution with dichloromethane to give trans-3-naphthalen-2-ylbicyclo[2.2.2]oct-5-ene-2-carbonitrile, M/e 260 (M+H$^+$).

Similarly prepared was:
cis-3-naphthalen-2-ylbicyclo[2.2.2]oct-5-ene-2-carbonitrile.

EXAMPLE 17

(2E)-3-(1H-indol-5-yl)-2-propenenitrile

To a stirred solution of 5-iodoindole (2.43 g, 10 mmol) in dry acetonitrile was added acrylonitrile (1.06 g, 20 mmol), followed by triethylamine (2.02 g, 20 mmol),Palladium acetate (66 mg, 0.3 mmol) and finally triphenylphosphine (156 mg, 0.6 mmol). The mixture was heated to reflux under N2 atmosphere for 6 hours. Since some starting material was remaining by TLC, more acrylonitrile (1.06 g, 20 mmol) was added and the reflux was carried on for a further 18 hours.

When cool, the solvent was evaporated to dryness, and the product was purified by column chromatography on flash silica with DCM to give a white solid as (2E)-3-(1H-indol-5-yl)-2-propenenitrile in 77% yield. M/e 169 (MH+).

EXAMPLE 18 trans-3-Naphthalen-2-ylbicyclo[2.2.2]octane-2-carbonitrile

To a solution of trans-3-naphthalen-2-ylbicyclo[2.2.2]oct-5-ene-2-carbonitrile (1.2 g) in ethyl acetate (50 ml) was added 10% Pd—C (120 mg). The reaction was hydrogenated at 60 psi using a Parr hydrogenator for 1 hour. The catalyst was removed by filtration through celite and the solvent removed by evaporation in-vacuo. The product was recrystallised from ethyl acetatehexane to give trans-3-naphthalen-2-ylbicyclo[2.2.2]octane-2-carbonitrile, Mp108–110° C.

Similarly prepared was:
cis-3-naphthalen-2-ylbicyclo [2.2.2]octane-2-carbonitrile.

EXAMPLE 19 trans-(3-Naphthalen-2-ylbicyclo[2.2 .2]oct-2-yl) methanamine

To a stirred solution of trans-3-naphthalen-2-ylbicyclo [2.2.2]octane-2-carbonitrile(1 g) in dry ether (30 ml) was added a solution of lithium aluminium hydride in tetrahydrofuran (174 mg). The reaction was heated at reflux for 2 hours. After cooling to room temperature water (1 ml) was added dropwise with caution followed by 2NNaOH (1 ml). When gas evolution ceased the reaction mixture was filtered through a pad of celite which was well washed with ether. After removal of the solvent in-vacuo the product was converted to the hydrochloride salt and re-crystallised from ethanolether to give trans-3-naphthalen-2-ylbicyclo[2.2.2] oct-2-yl)methanamine, mp272–274° C.

Similarly prepared, as hydrochloride or maleate salts, were:
cis-(3-naphthalen-2-ylbicyclo [2.2.2]oct-2-yl)methanamine
[(2R,3R)-3-(6-methoxy-2-naphthyl)bicyclo[2.2.2]oct-2-yl]-N,N-dimethylmethanamine, mp=218–220 C.
[(2R,3R)-3-(1H-indol-3-yl)bicyclo[2.2.2]oct-2-yl]-N,N-dimethylmethanamine, mp=132–134 C.
N,N-dimethyl[(2R,3R)-3-(2-naphthyl)bicyclo[2.2.2]oct-2-yl]methanamine, mp=126–128 C.
N,N-dimethyl[(2S,3S)-3-(2-naphthyl)bicyclo[2.2.2]oct-2-yl]methanamine, mp=128–130 C.
[(2R,3R)-3-(1-benzothien-5-yl)bicyclo[2.2.2]oct-2-yl]-N, N-dimethylmethanamine, mp=63–65 C.
[(2R,3R)-3-(1H-indol-5-yl)bicyclo[2.2.2]oct-2-yl]-N,N-dimethylmethanamine, mp=184–186 C.
N-methyl[(2R,3R)-3-(2-naphthyl)bicyclo[2.2.2]oct-2-yl] methanamine, mp=112–114 C.
N-methyl[(2S,3S)-3-(2-naphthyl)bicyclo[2.2.2]oct-2-yl] methanamine, mp=114–116 C.

EXAMPLE 20 trans-N, N-Dimethyl (3-naphthalen-2-ylbicyclo [2.2.2]oct-2-yl)methanamine

A mixture of trans-(3-naphthalen-2-ylbicyclo[2.2.2]oct-2-yl)methanamine (0.8, mole), 90% formic acid (5 ml) and 40% aqueous formaldehyde (5 ml) in dimethylformamide (10 ml) was heated at reflux for 2 hours. The reaction was poured into ice water and extracted with diethyl ether. The solvent was washed with brine, dried and evaporated to dryness in-vacuo. Chromatography on flash silica by elution with 10% methanol/dichloromethane followed by crystallisation of the hydrochloride salt from ethanol ether gave trans-N,N-dimethyl(3-naphthalen-2-ylbicyclo[2.2.2]oct-2-yl)methanamine, Mp236–238° C.

Similarly prepared was:
cis-N,N-dimethyl(3-naphthalen-2-ylbicyclo[2.2.2]oct-2-yl) methanamine.

EXAMPLE 21

Tablets each containing 10 mg of active ingredient are made up as follows:

| | |
|---|---:|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed on a tablet machine to yield tablets each weighing 300 mg.

EXAMPLE 22

Capsules each containing 20 mg of medicament are made as follows:

| Active ingredient | 20 mg |
|---|---|
| Dried starch | 178 mg |
| Magnesium stearate | 2 mg |
| Total | 200 mg |

The active ingredient, starch and magnesium stearate are passed through a sieve and filled into hard gelatine capsules in 200 mg quantities.

EXAMPLE 23

[$^3$H]-Citalopram Binding Assay

The ability of compounds of the invention to displace [$^3$H]-citalopram from binding sites on rat cerebral cortical membranes was measured in the following way:

In each well of a 96 deep well plate was added:

| 100 ml | 2 nM [$^3$H]-citalopram |
|---|---|
| 600 ml | 50 mM Tris.HCl pH 7.4 containing 150 mM NaCl and 5 mM KCl |
| 100 ml | Diluted compound, 50 mM Tris.HCl pH 7.4 containing 150 mM NaCl and 5 mM KCl (total binding) or 100 mM fluoxetine (non-specific binding) |
| 200 ml | Membrane preparation (0.75 mg protein per ml) |

The microtitre plates were incubated at 37° C. for 90 minutes followed by filtration through GFB filters soaked in 50 mM Tris.HCl/0.1% (wv) polyethylenimine pH 7.4. The filter was washed 5 times with 50 mM Tris.HCl. pH 7.4. The filters were removed, dried and the bound tritium determined by liquid scintillation spectrometry.

The results were analysed using an automatic spline fitting programme to provide Ki values for each of the compounds. By way of example, the following compounds had a $K_i$ of less than 100 nM:

trans-endo-N,N-dimethyl(3-naphthalen-2-ylbicyclo[2.2.1]hept-2-yl)methanamine trans-exo-N,N-dimethyl(3-naphthalen-2-ylbicyclo[2.2.1]hept-2-yl)methanamine cis- N,N-dimethyl(3-naphthalen-2-ylbicyclo[2.2.1]hept-2-yl)methanamine

[(1S,2S,3S,4R)-3-(6-fluoro-2-naphthyl)bicyclo[2.2.1]hept-2-yl]-N,N-dimethylmethanamine

[(1S,2S,3S,4R)-3-(1benzothien-6-yl)bicyclo[2.2.1]hept-2-yl]-N,N-dimethylmethanamine N-N-dimethyl[(1R,2R,3R,4S)-3-(3-methyl-1-benzothien-5-yl)bicyclo[2.2.1]hept-2-yl]methanamine

[(1S,2S,3S,4R)-3-(6-fluoro-1-benzothien-3-yl)bicyclo[2.2.1]hept-2-yl]-N,N-dimethylmethanamine

[(1S,2S,3S,4R)-3-(6-fluoro-1-benzothien-2-yl)bicyclo[2.2.1]hept-2-yl]-N,N-dimethylmethanamine trans-endo-N-methyl(3-naphthalen-2-yl)bicyclo[2.2.1]hept-2-yl)methanamine trans-(3-naphthalen-2-ylbicyclo[2.2.2]oct-2-yl)methanamine cis-(3-naphthalen-2-ylbicyclo[2.2.2]oct-2-yl)methanamine.

What is claimed is:

1. A compound of the formula

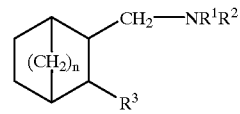

in which $R^1$ and $R^2$ are each hydrogen or $C_{1-4}$ alkyl, or $R^1$ and $R^2$ together with the nitrogen atom to which they are attached form an azetidinyl, pyrrolidinyl, piperidinyl, piperazinyl or morpholino group, said group being optionally substituted with 1 to 3 $C_{1-4}$ alkyl substituents, $R^3$ is a naphthyl, indolyl, benzothienyl, benzofuranyl, benzothiazolyl, quinolinyl or isoquinolinyl group, said group being optionally substituted, and n is 1 or 2; or a salt or ester thereof.

2. A compound according to claim 1, in which $R^1$ and $R^2$ are each hydrogen or $C_{1-4}$ alkyl, and $R^3$ is a naphthyl, indolyl, benzothienyl, benzofuranyl, benzothiazolyl, quinolinyl or isoquinolinyl group, said group being optionally substituted.

3. A compound according to either of claims 1 and 2, in which the naphthyl group is β-naphthyl.

4. A compound according to claim 1, in which $R^3$ is β-naphthyl, 2-,3-,5- or 6-indolyl, 2-,3-,5- or 6-benzothienyl, 2-,3-,5- or 6-benzofuranyl, 2- or 5-benzothiazolyl, 2-,3-,6- or 7-quinolinyl or 3-,6- or 7-isoquinolinyl, said group being optionally substituted.

5. A compound according to claim 4, in which $R^3$ is β-naphthyl, 2-,3-,5- or 6-indolyl, 2-,3-,5- or 6-benzothienyl or 2-,3-,5- or 6-benzofuranyl.

6. A compound according to claim 2, in which $R^3$ is β-naphthyl, optionally substituted with 1 to 3 substituents chosen from $C_{1-4}$ alkyl, $C_{1-4}$ alkoxy, carboxy, hydroxy, cyano, halo, trifluoromethyl, —NR'R" and —CONR'R" where R' and R" are each hydrogen or $C_{1-4}$ alkyl.

7. A compound according to any of claims 1 to 6, in which n is 1.

8. A compound according to claim 1 of the formula

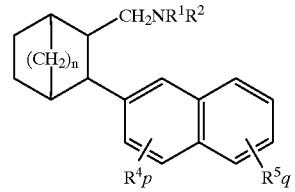

in which $R^1$ and $R^2$ are each hydrogen or $C_{1-4}$ alkyl, $R^4$ and $R^5$ are each $C_{1-4}$ alkyl, $C_{1-4}$ alkoxy, carboxy, hydroxy, cyano, halo, trifluoromethyl, -NR'R" or —CONR'R", where R' and R" are each hydrogen or $C_{1-4}$ alkyl, and p and q are each 0 or 1 to 3, such that the sum of p and q is 0 or 1 to 3; or a salt thereof.

9. A compound according to claim 8, in which p and q are both 0, and n is 1.

10. A compound according to claim 1, in which $R^3$ is 2-,3-,5- or 6-benzothienyl, optionally substituted with 1 to 3 substituents chosen from $C_{1-4}$ alkyl, $C_{1-4}$ alkoxy, carboxy, hydroxy, cyano, halo, trifluoromethyl, —NR'R" and —CONR'R" where R' and R" are each hydrogen or $C_{1-4}$ alkyl.

11. A compound according to claim 1 of the formula

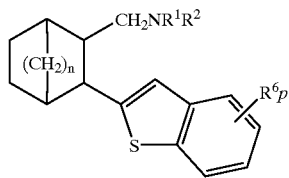

in which $R^1$ and $R^2$ are each hydrogen or $C_{1-4}$ alkyl, and $R^6$ is $C_{1-4}$ alkyl, $C_{1-4}$ alkoxy, carboxy, hydroxy, cyano, halo, trifluoromethyl, -NR'R" or -CONR'R", where R' and R" are each hydrogen or $C_{1-4}$ alkyl, and p is 0 or 1 to 3; or a salt thereof.

12. A compound according to claim 1 of the formula

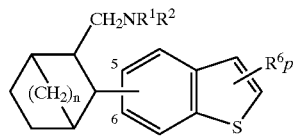

where the bicyclo group is attached at the 5- or 6-position, and in which $R^1$ and $R^2$ are each hydrogen or $C_{1-4}$ alkyl, and $R^6$ is $C_{1-4}$ alkyl, $C_{1-4}$ alkoxy, carboxy, hydroxy, cyano, halo, trifluoromethyl, —NR'R" or —CONR'R", where R' and R" are each hydrogen or $C_{1-4}$ alkyl, and p is 0, 1 or 2; or a salt thereof.

13. A compound of the formula

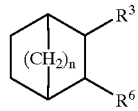

where $R^3$ and n have the values defined in claim 1, and $R^6$ is —$CONR^1R^2$, where $R^1$ and $R^2$ are each hydrogen or $C_{1-4}$ alkyl, or a salt thereof.

14. A pharmaceutical formulation comprising a compound according to claim 1 or a pharmaceutically acceptable salt or ester thereof, together with a pharmaceutically acceptable diluent or carrier therefor.

15. A compound according to claim 1, or a pharmaceutically acceptable salt or ester thereof, for use as a pharmaceutical.

16. A method of treating a disorder of the central nervous system which comprises administering an effective amount of a compound according to claim 1, or a pharmaceutically-acceptable salt or ester thereof.

* * * * *